(12) United States Patent
Kim

(10) Patent No.: US 9,149,203 B2
(45) Date of Patent: Oct. 6, 2015

(54) BLOOD SIGNAL SUPPRESSED ENHANCED MAGNETIC RESONANCE IMAGING

(75) Inventor: Raymond J. Kim, Durham, NC (US)

(73) Assignee: Duke University, Durham, NC (US)

( * ) Notice: Subject to any disclaimer, the term of this patent is extended or adjusted under 35 U.S.C. 154(b) by 316 days.

(21) Appl. No.: 13/100,272

(22) Filed: May 3, 2011

(65) Prior Publication Data

US 2011/0275928 A1    Nov. 10, 2011

Related U.S. Application Data

(60) Provisional application No. 61/331,567, filed on May 5, 2010.

(51) Int. Cl.
*A61B 5/055* (2006.01)
*G01R 33/56* (2006.01)

(52) U.S. Cl.
CPC ............ *A61B 5/055* (2013.01); *G01R 33/5602* (2013.01); *G01R 33/5607* (2013.01); *G01R 33/5601* (2013.01)

(58) Field of Classification Search
CPC .................................................. G01R 33/5607
USPC ......................................... 600/410, 413, 419
See application file for complete search history.

(56) References Cited

U.S. PATENT DOCUMENTS

| | | | |
|---|---|---|---|
| 5,297,550 A | 3/1994 | Margosian | |
| 5,422,576 A | 6/1995 | Kao et al. | |
| 6,205,349 B1 | 3/2001 | Kim et al. | |
| 6,340,887 B1 | 1/2002 | Liu et al. | |
| 6,397,096 B1 | 5/2002 | Liu et al. | |
| 6,498,946 B1 | 12/2002 | Foo et al. | |
| 6,526,307 B2 | 2/2003 | Foo | |
| 7,020,314 B1 | 3/2006 | Suri et al. | |
| 7,315,756 B2 | 1/2008 | Yarnykh et al. | |
| 7,941,204 B1 * | 5/2011 | Wang et al. | 600/420 |
| 8,086,297 B2 | 12/2011 | Rehwald et al. | |
| 2002/0016543 A1 * | 2/2002 | Tyler | 600/410 |
| 2002/0087067 A1 | 7/2002 | Foo | |
| 2003/0069493 A1 | 4/2003 | Pan et al. | |
| 2003/0069496 A1 * | 4/2003 | Foo | 600/413 |
| 2004/0049106 A1 | 3/2004 | Kanazawa | |
| 2004/0133098 A1 | 7/2004 | Yarnykh et al. | |

(Continued)

OTHER PUBLICATIONS

Chia-Ying Liu et al, Flow-Independent T2-prepared inversion recovery black-blood MR imaging, Dec. 20, 2009, vol. 31, Issue 1, pp. 248-254.*

(Continued)

*Primary Examiner* — Rochelle Turchen
(74) *Attorney, Agent, or Firm* — Olive Law Group, LLC

(57) ABSTRACT

Methods for achieving suppression of blood pool signal to image contrast-enhanced organs and vascular walls using magnetic resonance (MR) imaging technology. After administration of e.g., an intravenous contrast agent, an RF pulse sequence is applied that includes a preparatory section designed to modify signal from organ tissue differently than blood pool signal, followed by an inversion RF pulse. MR signals are then allowed to evolve during a wait time that is sufficiently long to permit tissue species with dissimilar T1 relaxation times to separate in signal yet short enough so that blood signal has greater negative magnetization than other tissues of interest. MRI data is then acquired with phase sensitive reconstruction so that blood pool signal is suppressed compared with the tissues of interest.

25 Claims, 3 Drawing Sheets

(56) References Cited

U.S. PATENT DOCUMENTS

| | | | |
|---|---|---|---|
| 2005/0215883 A1* | 9/2005 | Hundley et al. | 600/410 |
| 2005/0245809 A1 | 11/2005 | Wolff et al. | |
| 2006/0007429 A1 | 1/2006 | Emer et al. | |
| 2006/0074291 A1 | 4/2006 | Hardy et al. | |
| 2006/0099148 A1 | 5/2006 | Fisher et al. | |
| 2007/0038069 A1 | 2/2007 | Itagaki et al. | |
| 2007/0243136 A1 | 10/2007 | Fisher et al. | |
| 2009/0005673 A1* | 1/2009 | Rehwald et al. | 600/420 |
| 2010/0106007 A1* | 4/2010 | Wacker et al. | 600/420 |
| 2011/0260725 A1* | 10/2011 | Mordini et al. | 324/309 |

OTHER PUBLICATIONS

Edelman RR, et al. "Fast selective black blood MR imaging," Radiology, 1991;181(3):655-660 (1991).

Simonetti OP,et al, "Black blood T2-weighted inversion-recovery MR imaging of the heart," Radiology. 1996;199(1):49-57 (1996).

Yarnykh VL, et al, "T1-insensitive flow suppression using quadruple inversion recovery," Magn Reson Med. 2002;48(5):899-905 (2002).

Rehwald WG, et al, "Dark blood delayed enhancement in humans by double preparation and gradient-echo or turbo-spin-echo readout," Proc Intl Soc Magn Reson Med. (2007).

Salerno et al, "Contrast optimization of blackblood viability imaging," Proc Intl Soc Magn Reson Med. (2007).

Ibrahim El SH, et al, "Stimulated-echo acquisition mode (STEAM) MRI for black-blood delayed hyperenhanced myocardial imaging," J Magn Reson Imaging. 2008;27(1):229-238 (2008).

Kellman P, et al, "Multi-contrast delayed enhancement provides improved contrast between myocardial infarction and blood pool," J Magn Reson Imaging. 2005;22(5):605-613 (2005).

Liu CY, et al, "Improved delayed enhanced myocardial imaging with T2-Prep inversion recovery magnetization preparation," J Magn Reson Imaging. 2008;28(5):1280-1286 (2008).

Borrello JA et al, "Regional phase correction of inversion-recovery MR images," Magn Reson Med. 1990;14(1):56-67 (1990).

Xiang QS, "Inversion recovery image reconstruction with multiseed region-growing spin reversal," J Magn Reson Imaging. 1996;6(5):775-782 (1996).

Kim RJ, et al, "Relationship of MRI delayed contrast enhancement to irreversible injury, infarct age, and contractile function," Circulation. 1999;100(19) (1992-2002).

Foo, Thomas K., et al., "Enhanced Viability Imaginig: Improved Contrast in Myocardial Delayed Enhancement Using Dual Inversion Time Subtraction," Magnetic Resonance in Medicine 53:1484-1489 (2005).

Sievers, Burkhard, et al., "Rapid Detection of Myocardial Infarction by Subsecond, Free-Breathing Delayed Contrast-Enhancement Cardiovascular Magnetic Resonance," Circulation Journal of the American Heart Association (2007).

Schad, Lothar R., et al., "Magnetic Resonance Urography Using a Saturation Inversion Projection Spinecho Sequence," Magn Reson Imaging, p. 889, ncbi.nlm.nih.gov (1993).

Oesingmann, Niels, et al., "Optimization of a Saturation Inversion Projektion (SIP) Spin Echo (SE) Sequence for Magnetic Resonance Urography," Proceedings of the Society of Magnetic Resonance, vol. 1993, Issue S3, p. 1227 (1993).

Redpath, T.W., et al., A Double Inversion Recovery Sequence for Simultaneous Suppression of Lipid and Fluid Signals, p. 1194 (1987).

Gui, Dawei, et al., "Fast Magnetization-Driven Preparation for Imaging of Contrast-Enhanced Coronary Arteries During Intra-Arterial Injection of Contrast Agent," Journal of Magnetic Resonance Imaging 24:1151-1158 (2006).

Song, Hee Kwon, et al., "Multislice double inversion pulse sequence for efficient black-blood MRI," Magnetic Resonance in Medicine, vol. 47, issue 3, pp. 616-620 (Feb. 20, 2012).

Desai, Milind Y., et al., "Delayed Contrast-Enhanced MRI of the Aortic Wall in Takayasu's Arteritis: Initial Experience," American Journal of Roentgenology, 184: 1427-1431 (2005).

Berr, Stuart S., et al., "Black blood gradient echo cine magnetic resonance imaging of the mouse heart," Magnetic Resonance in Medicine, vol. 53, Issue 5, pp. 1074-1079 (Apr. 20, 2005).

Campos, S., et al., "New black blood pulse sequence for studies of the heart," The International Journal of Cardiac Imaging, vol. 15, No. 2 (Apr. 1999).

Klepac, Steven R., et al., "Cardiac MRI—Technical Aspects Primer," emedicine from WebMD, (Jul. 2005).

Rehwald, Wolfgang G., et al., "Myocardial Magnetic Resonance Imaging Contrast Agent Concentrations After Reversible and Irreversible Ischemic Injury," Circulation, Journal of the American Heart Association, pp. 224-229 (2002).

Simonetti, Orlando, et al., "2D and 3D Segmented TurboFLASH for the Visualization of Myocardial Injury," Proc. Intl. Soc. Mag. Reson. Med 8 (2000).

Simonetti, Orlando, et al., "An Improved MR Imaging Technique for the Visualization of Myocardial Infarction," Radiology 2001, vol. 218, No. 1, pp. 215-223 (2001).

McGill University, "Wiggers Diagram," pp. 1-2 (Jan. 3, 2000).

Albert, Timothy S.E., "Determining Myocardial Viability with MR Imaging," 38th Annual New York City Cardiovascular Symposium (Dec. 11, 2005).

Brittain, Jean H., et al., "Three-Dimensional Flow-Independent Peripheral Angiography," 1997 ISMRM Young Investigators' Moore Award Papers, 1997, MRM vol. 38, pp. 343-354.

Sharma, Puneet, et al., "Effect of Gd-DTPA-BMA on Blood and Myocardial T1 at 1.5T and 3T in Humans," Journal of Magnetic Resonance Imaging, 2006, vol. 23, pp. 323-330.

Kellman, Peter, et al., "Multicontrast Delayed Enhancement Provides Improved Contrast Between Myocardial Infarction and Blood Pool," Journal of Magnetic Resonance Imaging, 2005, vol. 22, pp. 605-613.

Liu, Chia-Ying, et al., "Improved Delayed Enhanced Myocardial Imaging With T2-Prep Inversion Recovery Magnetization Preparation," Journal of Magnetic Resonance Imaging, 2008, vol. 28, pp. 1280-1286.

Office Action dated Dec. 23, 2014, issued in related U.S. Appl. No. 13/302,259.

* cited by examiner

BLOOD SIGNAL SUPPRESSED ENHANCED MAGNETIC RESONANCE IMAGING

CROSS-REFERENCES TO RELATED APPLICATIONS

This application claims the benefit of priority from provisional application No. 61/331,567 filed May 5, 2010, incorporated herein by reference.

FIELD

The present disclosure relates generally to methods involving magnetic resonance imaging (MRI) technology, and more particularly to a new method to achieve improved imaging of organs and tissues by suppressing blood pool signal.

BACKGROUND

In Magnetic Resonance Imaging (MRI), contrast agents are often used to improve depiction of diseased from normal tissue. For instance, contrast agents may improve the sensitivity of MRI to identify myocardial infarction, stroke, tumors, atherosclerosis, tissue necrosis, and other diseased states. However, contrast agents may also increase blood pool signal. This may confound detection of abnormal tissue adjacent to blood. One example of this problem is in the setting of a myocardial infarction. Contrast-enhanced MRI is very useful in detecting myocardial infarction, and allows delineation of infarcted from non-infarcted regions by virtue of the fact that infarcted regions accumulate contrast media to a greater degree (see, e.g., Kim R. J. et al. (1999) *Circulation* 100: 1992-2002). Thus, on a T1-weighted MRI image after administration of a contrast agent with high R1 relaxivity, infarcted myocardium is usually bright (high image intensity) compared with non-infarcted myocardium. Unfortunately, the administration of contrast media also leads to high levels of contrast in the blood, and often it is difficult to delineate the border of infarcted myocardium from the blood in the heart chamber cavity. This may render the infarct undetectable, if small, or at a minimum make it difficult to accurately size the infarct. Another example is in the setting of vascular disease. Differences in contrast uptake within separate components of an atherosclerotic plaque is important to identify but may be difficult to detect since the blood within the lumen is immediately adjacent. These examples concern the cardiovascular system, however, the present disclosure may improve the depiction of diseased tissue from any organ system by suppressing blood pool signal.

Traditional "black-blood" MRI techniques have been in clinical use for several years, and are valued parts of the MRI armamentarium (see, e.g., Edelman, R. R. et al. (1991) *Radiology* 181:655-660; Simonetti, O. P. et al. (1996) *Radiology* 199:49-57). Moreover, these techniques have been improved to increase efficiency (see, e.g. U.S. Pat. Nos. 6,498,946 and 7,315,756). However, these techniques were not designed to image with the use of contrast media and the pulse sequence timing is usually based on the T1 of native blood without contrast media. Thus, these techniques were not intended to provide contrast-enhanced images of tissues, and not surprisingly, work poorly after the administration of contrast.

More recently, there have been several attempts to perform contrast-enhanced MRI with the suppression of blood pool signal. These include: (1) an MRI method and apparatus to improve myocardial infarction detection with blood pool signal suppression where the pulse sequence involves the use of a "notched" inversion RF pulse (see, e.g., U.S. Pat. No. 6,526, 307); (2) an MRI method to improve imaging of atherosclerotic plaque with suppression of blood signal where the pulse sequence employs a quadruple inversion-recovery (QIR) preparative pulse (see, e.g., Yarnykh, V. L. et al. (2002) *Magn. Reson. Med.* 48:899-905); (3) techniques for black-blood imaging of myocardial infarction (see, e.g., Rehwald, W. G. et al. (2007) *Proc. Intl. Soc. Magn. Reson. Med.* and Salerno, M. et al. (2007) *Proc. Intl. Soc. Magn. Reson. Med*; see also US 20090005673); and (4) MRI methods for black-blood delayed enhancement of myocardial imaging where the pulse sequence involves a stimulated-echo acquisition mode (STEAM) (see, e.g., Ibrahim, el S. H. et al. (2008) *J. Magn. Reson. Imaging* 27:229-238).

Of the above-enumerated methods, nos. 1-3 work by affecting the longitudinal magnetization of blood in regions outside of the imaged slice in a manner such that at the time when MR data is acquired, signal from blood outside of the imaged slice that flows into the specific region-of-interest is suppressed. Method 4 works in a different manner and behaves similar to spin-echo imaging with respect to blood flow. Irrespective of the specific mechanism, all of these methods are dependent on the speed of blood flow, and blood may be mistaken as part of the anatomy.

There have been also attempts to perform contrast-enhanced MRI with improved contrast between tissue and blood pool and yet in a manner that is independent of blood flow velocity. For example, Kellman et al. describe a multi-contrast MRI technique to improve contrast between myocardial infarction and blood pool by acquiring two separate images: a T2-weighted and a T1-weighted image (see, e.g., Kellman, P. et al. (2005) *J. Magn. Reson. Imaging* 22:605-613). Liu et al. describe a technique that is similar to that described by Kellman et al., but combines the weighting of T2 and T1 in a single image (see, e.g., Liu et al. (2008) *J. Magn. Reson. Imaging* 28: 1280-1286). Moreover, Foo et al. describe a dual inversion time subtraction method which utilizes two acquisitions at a long and short inversion time to improve delineation between the endocardial borders of an infarct from the ventricular blood pool (see, e.g., Liu, C. Y. et al. supra).

Although contrast between tissue and blood pool may be improved by some of the methods described in the paragraph above, the level of blood suppression may be minimal, and none of these methods are considered black-blood techniques. Specifically, these methods may result in images in which the signal of blood pool is higher than that of normal myocardium.

SUMMARY

The present disclosure relates to an MRI pulse sequence that produces black-blood, contrast-enhanced images of tissues and vascular walls.

In one aspect, the present disclosure provides a method of magnetic resonance imaging with blood signal suppression comprising administering a contrast agent to the patient; applying a pulse sequence having a preparatory section designed to modify signal from organ tissue differently than blood pool signal followed by an inversion RF pulse; waiting for a period of time that is sufficiently long to allow organ tissue with dissimilar T1 relaxation times to have disparity in signal, yet short enough so that blood signal has greater negative magnetization than the tissues of interest: and acquiring MRI data from the region-of-interest with a phase sensitive reconstruction.

In certain embodiments, the preparatory section comprises one or more RF pulses that imparts weighting from the group consisting of T2, T1rho or magnetization transfer weighting and combinations thereof. In one embodiment, the preparatory section comprises one or more RF pulses that imparts T2 weighting. In other embodiments, the preparatory section comprises one or more RF pulses that imparts T1rho weighting. On yet another embodiment, the preparatory section comprises one or more RF pulses that imparts magnetization transfer weighting.

In other embodiments, the inversion RF pulse has a flip angle between 90 and 180 degrees.

In other embodiments, the MRI data is acquired using a technique selected from the group consisting of a steady-state free precession (SSFP), a gradient-recalled echo (GRE) readout, a turbo-spin echo (TSE) readout, an echo planar (EPI) readout, a 2-dimensional readout, a 3-dimensional readout, a segmented acquisition such that data acquired for an image comes from at least two cycles of the sequence, a single-shot acquisition so that data acquired for an image comes from one cycle of the sequence, parallel imaging, Cartesian readout, radial readout, spiral readout, or elliptical readouts and combinations thereof.

In another embodiment, the readout is timed to occur during a specific phase of the electrocardiogram. In other embodiments, the phase sensitive reconstruction is based on obtaining a reference set of the data. In other embodiments, the phase sensitive reconstruction is based on estimating the phase from local statistics or region growing approaches.

Other example non-limiting advantages of example implementations herein include:
  not dependent on the blood flow velocity
  is a black-blood technique and results in a blood pool signal that is lower than all the other tissues of interest
  not dependent on the particular PSIR method chosen.

BRIEF DESCRIPTION OF THE DRAWINGS

Other advantages and novel features of the present disclosure will become apparent from the following detailed description of various non-limiting embodiments of the disclosure when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

The accompanying drawings are not intended to be drawn to scale. In the drawings, each identical or nearly identical component that is illustrated in various figures is represented by a like numeral. For purposes of clarity, not every component is labeled in every drawing. The foregoing objects, features and advantages of the present disclosure will become more apparent from a reading of the following description in connection with the accompanying drawings in which.

DETAILED DESCRIPTION OF EXAMPLE EMBODIMENTS

Figure 1:
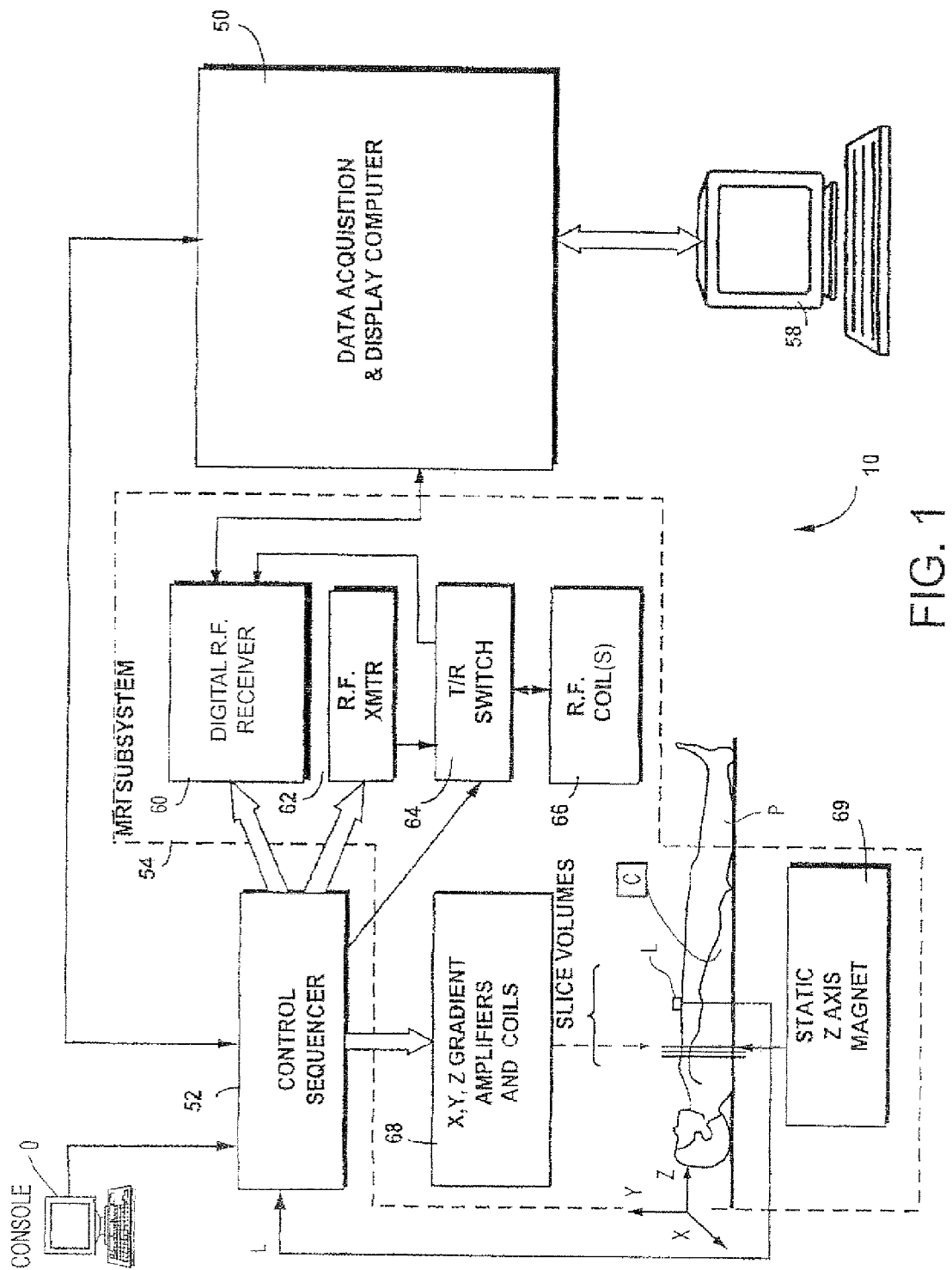
FIG. 1 shows an example MRI system.

The present disclosure is not limited in its application to the details of construction and the arrangement of components set forth in the following description or illustrated in the drawings. The technology described in the present disclosure is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items. For the purposes of promoting an understanding of the principles of the present disclosure, reference will now be made to preferred embodiments and specific language will be used to describe the same.

Articles "a," "an," and "the" are used herein to refer to one or to more than one (i.e. at least one) of the grammatical object of the article. By way of example, "an element" means at least one element and can include more than one element. Similarly, reference to "a cell" includes a plurality of cells, and in some embodiments, can include a tissue and/or an organ.

While the following terms are believed to be well understood by one of ordinary skill in the art, the following definitions are set forth to facilitate explanation of the presently disclosed subject matter. Although any methods, devices, and materials similar or equivalent to those described herein can be used in the practice or testing of the presently disclosed subject matter, representative methods, devices and materials are now described.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In certain embodiments, the subject is a human patient.

As used herein, the term "contrast agent" refers to any of the known contrast media used to improve the visibility of internal body structures in MRI that alter the relaxation times of tissues and body cavities where they are present, which depending of the image weighting can give a higher or lower signal. Examples include: (1) paramagnetic contrast agents, such as Gadolinium, and include, but are not limited to, gadodiamide, gadobenic acid, gadopentetic acind, gadoteridol, gadofosveset, gadoversetamide, gadoxetic acid, gadobutrol, gadocoletic acid, gadodenterate, gadomelitol, gadopenamide, and gadoteric acid; (2) superparamagentic contrast agents, such as iron oxide and include, but are not limited to, Cliavist, Combidex, Endorem (Feridex), Resovist, Sinerem, and the like; (3) paramagnetic contrast agents such as manganese, and include, but are not limited to, Mn-DPDP and the like; and (4) oral contrast agents, including but not limited to, gadolinium and manganese chelates or iron salts for T1 signal enhancement, SPIO, barium sulfate, air and clay for T2 signal enhancement, natural products with high manganese concentration such as blueberry and green tea can be used for T1 increasing contrast enhancement, Perflubron, and the like. In preferred embodiments, the contrast agent is a T1 agent with high R1 relaxivity.

Description of Embodiments

FIG. 1 shows an example magnetic resonance imaging ("MRI") system 10 including a data acquisition and display computer 50 coupled to an operator console O, a MRI real-time control sequencer 52, and a MRI subsystem 54. MRI subsystem 54 includes XYZ magnetic gradient coils and associated amplifiers 68, a static Z-axis magnet 69, a digital RF transmitter 62, a digital RF receiver 60, a transmit/receive switch 64, and RF coil(s) 66. As is well known, a dedicated cardiac or torso phased-array coil is typically used for cardiac imaging.

Electrocardiogram (ECG) leads L may be used in cardiac imaging to synchronize control sequencer 52 with electrical stimulation of the heart by the brain. The patient may or may not have electrodes L placed for electrocardiographic (ECG) gating. Generally, ECG gating will be useful for examinations of the cardiovascular system. However, ECG gating is not necessary if a single-shot version of the sequence below is used (e.g., data acquired for an image comes from one cycle of the sequence), or if motion of the organ or tissues of interest are minor.

Subsystem 54 is controlled in real time by sequencer 52 to generate magnetic and radio frequency fields that stimulate nuclear magnetic resonance ("NMR") phenomena in an object P (e.g., a human body) to be imaged. Specifically, in step 110 of FIG. 2, contrast media is administered to the patient. The contrast agent should preferably be a T1 agent with high R1 relaxivity. A suitable well known contrast agent (C) such as for example a T1 agent is injected intravenously into the patient P in a well known manner. A resulting image of patient P on display 58 shows features and structures that cannot be seen using X-ray, ultrasound or other medical imaging techniques. In the exemplary illustrative non-limiting implementation, the resulting dark or black blood myocardial viability imaging shows blood and healthy myocardium as black or dark and shows infarcts (including subendocardial infarcts) as bright.

Figure 2:
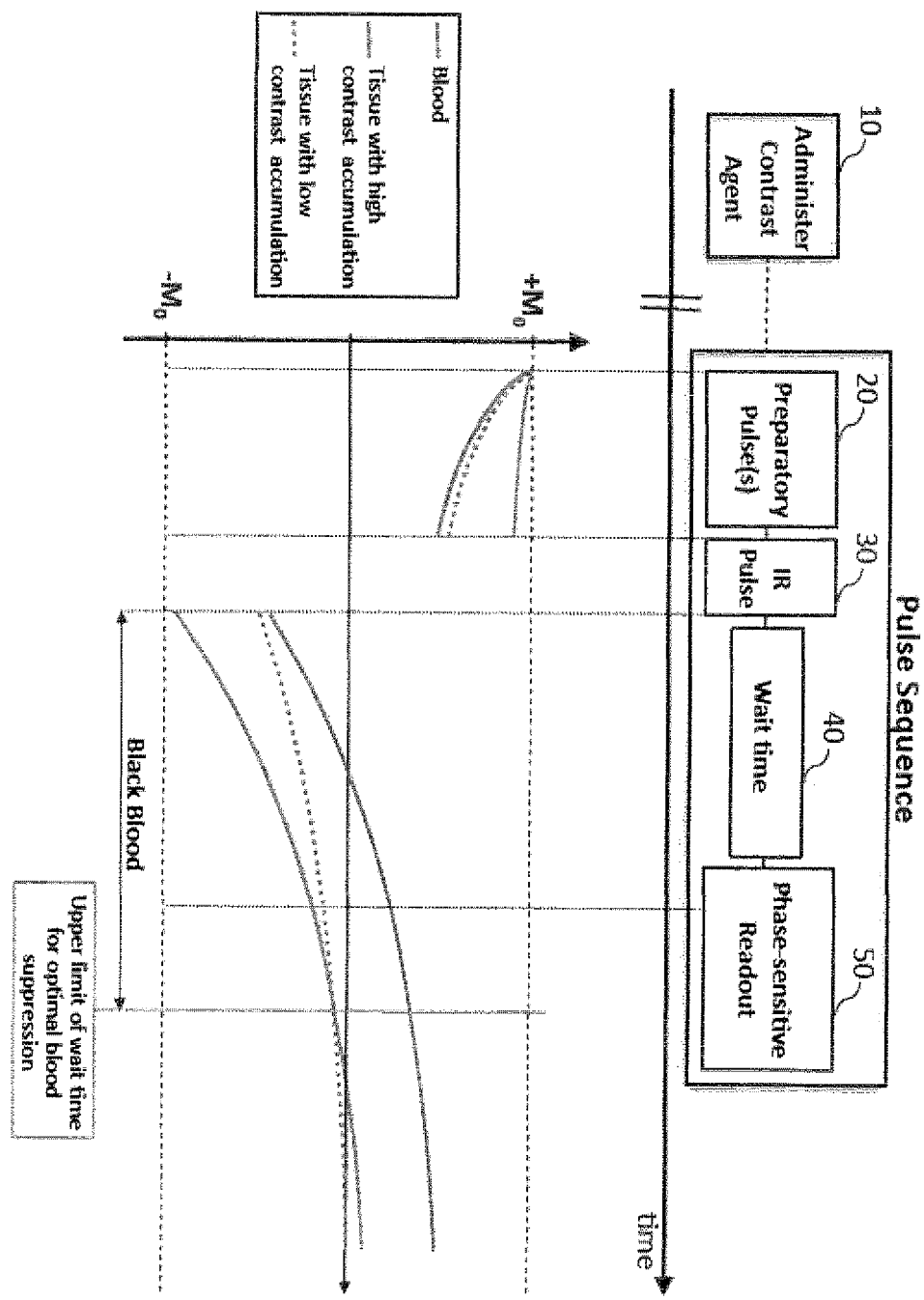
FIG. 2 is a schematic diagram of the MRI pulse sequence illustrating relative temporal positions of various components as well as the evolution of magnetization of blood and tissue.

Referring to FIG. 2, details of an example data acquisition pulse sequence and associated method are shown. The example pulse sequence consists of the following steps. First, one or more RF pulses are applied as part of a preparatory section 120. The goal of this section is to reduce tissue magnetization more than blood magnetization. This may be accomplished in many possible ways, include, but not limited to, the use of one or more RF pulses that imparts T2 weighting, or T1 rho weighting (longitudinal relaxation in the rotating frame), or magnetization transfer weighting, or a combination of these weightings, or by other weightings. By the end of this section, the magnitude of tissue magnetization should be less than blood magnetization. Second, a non-selective inversion pulse is applied 130. The goal of this section is to result in blood magnetization that is more negative (e.g., closer to $-M_0$) than the other tissues of interest. Third, a wait time interval occurs 140. This wait time is selected so that it is sufficiently long to permit tissue species with dissimilar T1 relaxation times to separate in signal. In general, diseased tissue will have more contrast agent accumulation than normal tissue and thus will have a steeper inversion recovery curve, however, the technology herein will work if diseased tissue has less contrast agent accumulation than normal tissue.

FIG. 2 shows an example plot of magnetization (from $-M_0$ to $+M_0$ on the vertical axis and time on the horizontal axis). The top curve in the upper left-hand corner (during preparatory pulse(s)) represents the magnetization of blood, the dotted curve represents magnetization of tissue with low contrast accumulation, and the solid curve beneath the dotted curve represents magnetization of tissue with high contrast accumulation. Note the appearance of black blood during the wait time after the IR pulse. This black blood condition extends into phase-sensitive readout. A vertical line on the right-hand side of the plot indicates the upper limit of wait time for optimal blood suppression, where the magnetization of blood intersects the magnetization curve for tissue with low contrast accumulation.

It is useful that tissue components have a disparity in contrast accumulation. Another constraint on the selection of the wait time is that it should be short enough so that the blood magnetization remains more negative than the other tissues of interest. This will allow the exemplary implementation to produce a black blood image. If the wait time is longer, the magnetization of blood may cross the inversion recovery curve of one or more tissue species. Collecting MRI data at this point will still result in partial blood suppression, but may not result in a black-blood image. The final component is to acquire MRI data in a phase-sensitive manner 150. That is to say, that signal polarity following the inversion pulse is to be retained rather than lost as in a conventional magnitude reconstruction, and image intensity should be proportional to the physical magnetization. There are numerous ways to perform a phase sensitive inversion recovery (PSIR) reconstruction. One example approach would be to calibrate the phase through acquisition of a background reference image without an inversion pulse (or long after the inversion pulse) (see, e.g., Rehwald, W. G., supra). Another would be to estimate the phase from the image itself using local statistics (see, e.g., Borrello, J. A. et al. (1990) *Magn. Reson. Med.* 14:56-67; Xiang, Q. S. et al., (1996) *J. Mag. Reson. Imaging* 6:775-782).

Figure 3:
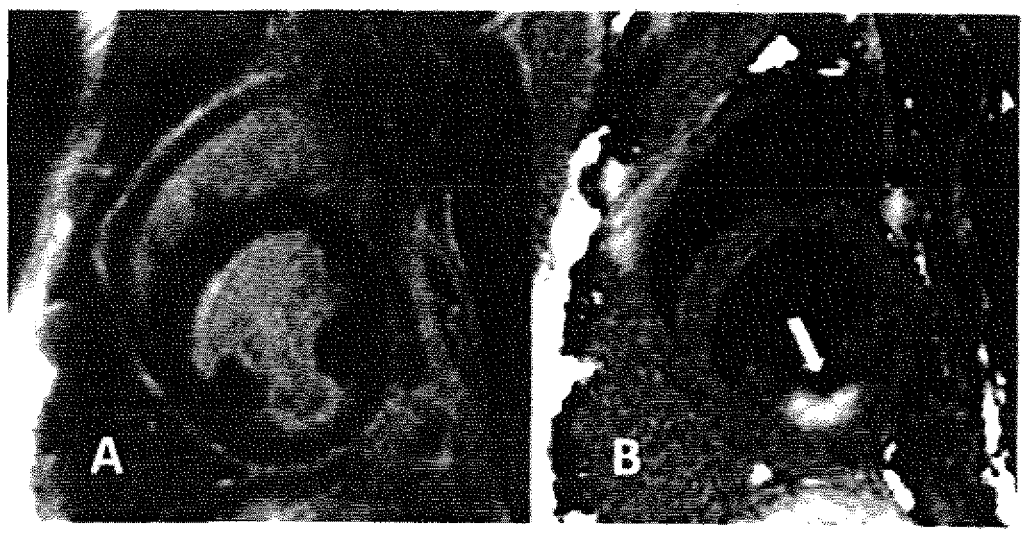
FIG. 3 are graphic images demonstrating a comparison between cardiac images acquired using a traditional delayed contrast-enhanced MRI technique (panel A) with images acquired with an implementation of the methods according to the present disclosure (panel B). The arrow points to the area of myocardial infarction.

FIG. 3 shows sample images obtained from a subject with a myocardial infarction approximately 20 minutes after administration of 0.15 mmol/kg of gadoversetamide. A traditional delayed enhancement MRI image is shown in panel A. A blood signal suppressed contrast-enhanced image using the methods described in the present disclosure is shown in panel B. The traditional sequence results in a bright-blood image, whereas the image produced using methods according to the present disclosure results in a black-blood image. Furthermore, the subendocardial border between the infarct (arrow) and the left ventricular blood pool is easily discernable using the methods of the present disclosure but is not visible on the traditional image. As shown in FIG. 3, the methods of the present disclosure are particularly useful in improving the visualization of myocardial infarction. As already indicated, however, the present disclosure is not limited to imaging the heart, and will be useful in imaging any tissue or organ in which suppressing blood signal will improve discernment of anatomy and or diseased tissue.

One skilled in the art will readily appreciate that the present disclosure is well adapted to carry out the objects and obtain the ends and advantages mentioned, as well as those inherent therein. The methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

While the technology herein has been described in connection with exemplary illustrative non-limiting embodiments, the invention is not to be limited by the disclosure. The invention is intended to be defined by the claims and to cover all corresponding and equivalent arrangements whether or not specifically disclosed herein.

I claim:

1. A method of black-blood magnetic resonance imaging (MRI) with blood signal suppression that is independent of blood flow velocity and blood exchange, comprising:
   a. administering an MRI contrast agent;
   b. waiting for the MRI contrast agent to arrive at the organ tissue of interest; then
   c. using an RF transmitter, applying an RF pulse sequence having (i) a preparatory section that reduces the MRI magnetization of the organ tissue more than the MRI magnetization of blood pool, and (ii) following the preparatory section with an inversion RF pulse;
   d. after applying the RF pulse sequence, waiting for a period of time which is independent of blood flow, the wait time period selected so that (i) the MRI magnetization of healthy organ tissue will be different than the MRI magnetization of diseased organ tissue due to differences in organ tissue accumulation of the MRI contrast agent, and (ii) the MRI magnetization of blood pool will have a more negative signal vector than the MRI magnetization of healthy organ tissue;
   e. after waiting the period of time, acquiring magnetic resonance data from the organ tissue of interest; and
   f. generating a black blood image based on said acquired magnetic resonance data with a phase sensitive reconstruction.

2. The method according to claim 1, wherein the preparatory section comprises one or more RF pulses that imparts weighting selected from the group consisting of T2 weighting, T1rho weighting, magnetization transfer weighting, and combinations thereof.

3. The method according to claim 1, wherein the preparatory section comprises one or more RF pulses that imparts T2 weighting.

4. The method according to claim 1, wherein the preparatory section comprises one or more RF pulses that imparts T1rho weighting.

5. The method according to claim 1, wherein the preparatory section comprises one or more RF pulses that imparts magnetization transfer weighting.

6. The method according to claim 1, wherein the inversion RF pulse comprises a flip angle between 90 and 180 degrees.

7. The method of claim 1 wherein acquiring uses a steady-state free precession (SSFP).

8. The method of claim 1 wherein acquiring uses a gradient-recalled echo (GRE) readout.

9. The method of claim 1 wherein acquiring uses a turbo-spin (TSE) readout.

10. The method of claim 1 wherein acquiring uses an echo planar (EPI) readout.

11. The method of claim 1 wherein acquiring uses a 2-dimensional readout.

12. The method of claim 1 wherein acquiring uses a 3-dimensional readout.

13. The method of claim 1 wherein acquiring uses a segmented acquisition so that data acquired for an image comes from at least two cycles of the pulse sequence.

14. The method of claim 1 wherein acquiring uses a single-shot acquisition so that data acquired for an image comes from once cycle of the pulse sequence.

15. The method of claim 1 wherein acquiring uses parallel imaging.

16. The method of claim 1 wherein acquiring uses a Cartesian, radial, spiral or elliptical readout.

17. The method according to claim 1, wherein acquiring uses a technique comprising at least one of gradient-recalled echo (GRE) readout, turbo-spin echo (TSE readout, echo planar (EPI) readout, 2-dimensional readout, 3-dimensional readout, segmented acquisition so that data acquired for an image comes from at least two cycles of the pulse sequence, a single-shot acquisition so that data acquired for an image comes from one cycle of the pulse sequence, parallel imaging, Cartesian readout, radial readout, spiral readout, elliptical readout, and combinations thereof.

18. The method according to claim 1, further including timing readout to occur during a specific phase of an electrocardiogram after the wait time period expires.

19. The method according to claim 1, wherein the phase sensitive reconstruction is also based on obtaining a reference set of data.

20. The method according to claim 1, wherein the phase sensitive reconstruction is also based on estimating the phase from local statistics or region growing approaches.

21. The method of claim 1 wherein the preparatory section is not required to have any slice-selective RF pulses.

22. The method of claim 1 wherein the preparatory section does not have any slice-selective RF pulses.

23. A system for black-blood magnetic resonance imaging (MRI) when administering an MRI contrast agent and waiting for the MRI contrast agent to arrive at the organ tissue of interest, the system providing blood signal suppression that is independent of blood flow velocity and blood exchange, the system comprising:
   an RF transmitter configured to apply an RF pulse sequence having (i) a preparatory section that reduces the MRI magnetization of the organ tissue more than the MRI magnetization of blood pool, and (ii) an inversion RF pulse following the preparatory section;
   a sequencer coupled to the RF transmitter that, after controlling the RF transmitter to apply the pulse sequence, is configured to wait a wait time period which is independent of blood flow, the wait time period selected so that (i) the MRI magnetization of healthy organ tissue will be different than the MRI magnetization of diseased organ tissue due to differences in organ tissue accumulation of the MRI contrast agent, and (ii) the MRI magnetization of blood pool will have a more negative signal vector than the MRI magnetization of healthy organ tissue;
   an RF receiver coupled to the sequencer, the receiver acquiring magnetic resonance data after waiting the selected wait time period; and
   at least one computer operatively coupled to the RF receiver, the computer using a phase sensitive reconstruction to generate a black blood image based on said acquired magnetic resonance data the RF receiver acquires after the sequencer waits the wait time period.

24. The system of claim 23 wherein the RF transmitter is configured to generate the preparatory pulse signal without any slice-selective RF pulses.

25. The system according to claim 23, wherein sequencer times the receiver to acquire the magnetic resonance echoes during a specific phase of an electrocardiogram after the wait time period has expired.

* * * * *